US00PP13106P2

(12) United States Plant Patent
Carruth

(10) Patent No.: US PP13,106 P2
(45) Date of Patent: Oct. 22, 2002

(54) FLORIBUNDA ROSE PLANT NAMED 'WEKGIBOTEX'

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 8 days.

(21) Appl. No.: 09/715,340

(22) Filed: Nov. 17, 2000

(51) Int. Cl.[7] ..... A01H 5/00
(52) U.S. Cl. ..... Plt./145
(58) Field of Search ..... Plt./145

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of Floribunda rose suitable for garden decoration, having flowers of yellow coloration.

1 Drawing Sheet

BOTANICAL CLASSIFICATION

*Rosa hybrida.*

VARIETY DENOMINATION

'Wekgibotex'.

BACKGROUND OF THE INVENTION

This invention relates to a new and distinct variety of Floribunda Rose. The varietal denomination of the new variety is *Rosa hybrida* cv. 'WEKgibotex'. It has as its seed parent an undistributed seedling of my creation and as its pollen parent a different undistributed seedling of my creation.

SUMMARY OF THE INVENTION

Among the features which distinguish the new variety from other presently available and commercial rose cultivars known to the inventor are the following combination of characteristics: its almost entirely smooth peduncle and bud surface, its continuity of yellow color from the fresh to the older flower and its suffusion of red pigmentation in the styles. The plant has a rounded bushy growth habit, suitable for outdoor garden decoration.

Asexual reproduction of the new variety by budding as performed in Kern County and Upland, Calif., shows that the foregoing and other distinguishing characteristics come true to form and are established and transmitted through succeeding propagations. 'WEKgibotex' may be asexually propagated by cuttings, budding and grafting.

COMPARISON WITH PARENTS

The new rose may be distinguished from its seed parent, an undisseminated seedling of my creation, by the following combination of characteristics: whereas 'WEKgibotex' bears medium sized flowers (about 6.6 to about 9.5 cms. in diameter) with double petalage (about 19 to about 29), the seed parent bears significantly larger flowers (about 9 to about 11 cms. in diameter) with heavier petalage (about 28 to about 38). The seedling parent has a bushy upright mature growth habit, whereas the new variety has a very rounded bushy mature growth habit.

The new variety may be distinguished from its pollen parent, an undisseminated seedling of my creation, by the following combination of characteristics: whereas 'WEKgibotex' bears medium sized flowers with double petalage as described above, the pollen parent bears significantly smaller flowers (about 5.5 to about 7.5 cms. in diameter) with lower petalage (about 12 to about 18). The pollen parent bears foliage with a matte finish, whereas 'WEKgibotex' bears foliage with a semi-glossy finish.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon The Colour Chart of The Royal Horticultural Society of London, England, (1995 ed.) except where common terms of color definition are employed.

DESCRIPTION OF THE NEW VARIETY

The following description is of 3 to 4 year old rose plants of the new cultivar grown outdoors in Upland, Calif. in the month of October. Phenotypic expression may vary with environmental, cultural and climatic conditions, as well as differences in conditions of light and soil. As indicated by the USDA Plant Hardiness Zone Map, the plant's winter hardiness is between zones 5b and 6a. The plant's drought/heat tolerance is yet to be determined. Root initiation can vary between about 10 to 21 days. Temperature, age of the cutting wood and time of the year are variables.

FLOWER

The new variety usually bears its flowers singly, sometimes in clusters of two to three or more per stem. Flowers are borne in somewhat irregular clusters on short to medium length stems (about 14 to about 29 cms.). Outdoors, the plant blooms abundantly and nearly continuously during the growing season. The flowers have a moderate fruity fragrance. The petiole is about 0.8 to about 1.2 cm in length and about 0.1 to about 0.2 cm in diameter at the widest point. The petiole color is near 138B.

BUD

The peduncle is about 2.4 to about 5.3 cms. in length, of slender to average caliper and usually erect. It is almost entirely smooth. Peduncle color is between 138B and 144B.

Before the calyx breaks, the bud is about 0.9 to about 1.6 cms. in diameter at the widest point, about 1.4 to about 2.0 cms. in length and very pointed to ovoid in shape. The surface of the bud bears few slender foliaceous appendages and very few stipitate glands, usually with slender foliaceous parts extending beyond the tip of the bud about ¼ or more of its length. Bud color is between 138B and 144B.

The inner surface of the sepals is covered with fine wooly tomentum; sepal margins are lined with some stipitate glands and hairs.

As the petals open (after the calyx breaks), the bud is about 1.6 to about 2.5 cms. in diameter at the widest point, about 2.2 to about 2.8 cms. in length, and pointed to ovoid in form. The color of the under surfaces of the newly opened petals is between 13C and 15C. At the point where the petal attaches, there is a medium sized zone of near 1B. The color of the upper surfaces of the newly opened petals is between 13A and 13C. At the point where the petal attaches, there is a moderately small zone of near 1B.

BLOOM

When fully open, the bloom ranges from about 6.6 to about 9.5 cms. in diameter. Petalage is double with about 19 to 29 petals and about 4 to 10 petaloids arranged irregularly. When partially open, the bloom form is moderately cupped to high centered and the petals are somewhat loosely spiraled with petal edges slightly reflexed outward. When fully open, the bloom form is more cupped to somewhat flat and the petals are moderately cupped with petal edges more reflexed outward.

PETALS

The substance of the petals is moderately thick, with upper surfaces moderately satiny and under surfaces slightly shiny to somewhat matte. The outer petals are nearly round to broadly obovate in shape with rounded apices. The inner petals are more broadly obovate in shape with round apices. The petal margin is entire. Petals are about 2.4 to about 4.0 cm in length and about 2.3 to about 3.8 cm in width at the widest point.

NEWLY OPENED FLOWER

The under surface of the outer, intermediate and inner petals is between 13C and 11A. The upper surface of the outer, intermediate and inner petals is between 12A and 11B. There is no change of coloration at the point where the petal attaches.

The general tonality of the newly opened flower is between 11B and 12A.

THREE-DAY-OLD FLOWER

The under surface of the outer and inner petals is between 11C and 10B. The upper surface of the outer and inner petals is between 10A and 11B. There is no change of coloration at the point where the petal attaches.

The general tonality of the three-day-old flower is between 10A and 11B.

On the spent bloom, the petals usually drop off cleanly.

In October in Upland, Calif. blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 135) and are arranged regularly about the pistils; a few are mixed with petaloids. The filaments are irregular in length, most with anthers. Filaments are between 15A and 17C in color sometimes blushed at the base with near 42A. The anthers open approximately at the same time. Anther color is between 15C and 13A when immature and between 165B and 167B at maturity. Pollen is very abundant and near 14D in color.

FEMALE REPRODUCTIVE ORGANS

Pistils vary in number (average about 75). The styles are moderately uneven, somewhat average in caliper and moderately bunched. Stigma color is near 23D. Style color is between 1C and 3C usually blushed on the upper portion with between 53B and 46B. Ovaries are usually all enclosed in the calyx.

Hips are somewhat short to average in lengh, somewhat flat to globular in form, and near 28A in color when ripe. The hip surface is very smooth with moderately thick fleshy walls. The The sepals are usually permanent. There are approximately 15 to 21 seeds, moderately large in size.

FOLIAGE

The compound leaves are usually comprised of three to five or more leaflets and are borne abundantly. The five-leaflet leaves are about 6.4 to about 9.4 cms. in length and about 4.6 to about 6.1 cms. in width at the widest point, moderately leathery in texture and somewhat semi-glossy in finish. The terminal leaflets are about 3 to about 4.1 cms. in length and about 2.0 to about 2.6 cms. in width at the widest point, shaped oval with acute apices and moderately acute to somewhat rounded bases. Their margins are usually simply serrate.

The upper surface of the mature leaf is between 136B and 137A. The under surface of the mature leaf is near 138B. The upper and under surface of the young leaf is between 144A and 144C, sometimes lightly suffused especially at the leaf margin with as dark as between 183C and 187D.

The rachis is somewhat light in caliper and very smooth. The upper side is moderately grooved with some hairs and few stipitate glands on the edges of the grooves. The under side of the rachis is almost entirely smooth.

The stipules are about 0.6 to about 1.2 cms. in length and somewhat narrow to medium width with short straight points that usually turn out at an angle of less than 90 degrees.

The plant displays an above average degree of resistance to powdery mildew and rust as compared to other commercial varieties grown under comparable conditions in Upland, Calif.

GROWTH

The plant has a bushy rounded medium height growth habit (about 95 to about 110 cms. in height and equal in spread at the widest point), with very full branching. It displays moderately vigorous growth and the canes are somewhat light to medium caliper for the class. The sepals are about 1.7 to about 3.0 cm in length and about 0.7 to about 1.0 cm in width at the widest point. The under surface of the sepal is between 138B and 144B . The upper surface of the sepal is between 139C and 148D.

The color of the major stems is near 146C. They bear very few large prickles that are about 0.6 to about 1.0 cms. in length. The large prickles are almost straight and angled slightly downward with a moderately broad oval base; prickle color is between 165A and 165B. The major stem bears no small prickles.

The color of the branches is between 139C and 146B. The branch bears very few large and small prickles of similar shape; prickle color is between 160A and 161A.

The color of the new shoots is between 144A and 139C sometimes lightly suffused with as dark as between 183C and 187D. The new shoots bear very few large and small prickles of similar shape; prickle color is between 160A and 161A.

I claim:

1. A new and distinct Floribunda rose plant of the variety substantially as described and illustrated herein.

* * * * *

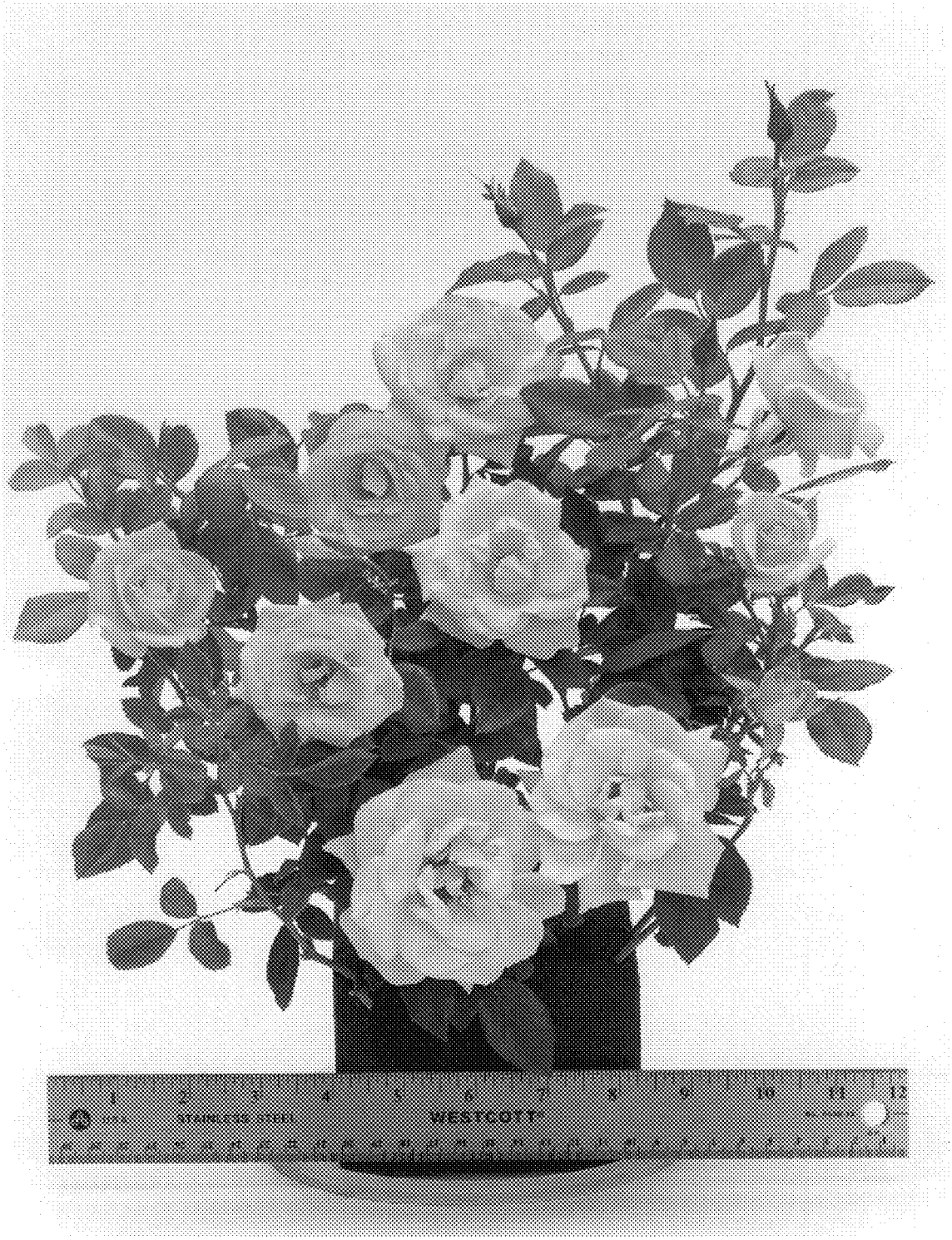
WESTCOTT